United States Patent
Tamura et al.

(10) Patent No.: US 9,425,021 B2
(45) Date of Patent: Aug. 23, 2016

(54) X-RAY GENERATION APPARATUS AND X-RAY RADIOGRAPHIC APPARATUS

(75) Inventors: Miki Tamura, Kawasaki (JP); Tamayo Hiroki, Zama (JP); Shigeki Matsutani, Sagamihara (JP); Takao Ogura, Yokohama (JP); Kazuyuki Ueda, Tokyo (JP); Yoshihiro Yanagisawa, Fujisawa (JP); Ichiro Nomura, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 142 days.

(21) Appl. No.: 14/241,817

(22) PCT Filed: Aug. 29, 2012

(86) PCT No.: PCT/JP2012/072518
§ 371 (c)(1),
(2), (4) Date: Feb. 27, 2014

(87) PCT Pub. No.: WO2013/032017
PCT Pub. Date: Mar. 7, 2013

(65) Prior Publication Data
US 2014/0192957 A1 Jul. 10, 2014

(30) Foreign Application Priority Data

Aug. 31, 2011 (JP) .................................. 2011-189109

(51) Int. Cl.
*H01J 35/08* (2006.01)
*H01J 35/14* (2006.01)
(Continued)

(52) U.S. Cl.
CPC ................ *H01J 35/08* (2013.01); *G01N 23/04* (2013.01); *H01J 35/14* (2013.01); *H01J 35/16* (2013.01);
(Continued)

(58) Field of Classification Search
CPC ............... G01N 23/04; H01J 2235/087; H01J 2235/168; H01J 2235/186; H01J 35/08; H01J 35/14; H01J 35/16; H05G 1/70
See application file for complete search history.

(56) References Cited

U.S. PATENT DOCUMENTS

| 4,159,437 A * | 6/1979 | Sahores ................. H01J 35/18 378/140 |
| 6,661,876 B2 * | 12/2003 | Turner ................. G01N 23/223 313/553 |

(Continued)

FOREIGN PATENT DOCUMENTS

| JP | 09171788 A | 6/1997 |
| JP | 11144653 A | 5/1999 |

(Continued)

OTHER PUBLICATIONS

Jensen, Charles, et al., "Improvements in Low Power, End-Window, Transmission-Target X-Ray Tubes" International Centre for Diffraction Data 2004, Advances in X-ray Analysis, vol. 47.*

*Primary Examiner* — Wyatt Stoffa (74) *Attorney, Agent, or Firm* — Canon USA Inc. IP Division (57) ABSTRACT

In an X-ray generation apparatus of transmission type including an electron emission source, and a target generating an X-ray with collision of electrons emitted from the electron emission source against the target, the X-ray generation apparatus further includes a secondary X-ray generation portion generating an X-ray with collision of electrons reflected by the target against the secondary X-ray generation portion, and the secondary X-ray generation portion and the target are arranged such that the X-ray generated with the direct collision of the electrons against the target and the X-ray generated with the collision of the electrons reflected by the target against the secondary X-ray generation portion are both radiated to an outside. X-ray generation efficiency is increased by effectively utilizing the electrons reflected by the target.

44 Claims, 7 Drawing Sheets

(51) Int. Cl.
  *H01J 35/16* (2006.01)
  *G01N 23/04* (2006.01)
  *H05G 1/70* (2006.01)
(52) U.S. Cl.
  CPC ............ *H05G 1/70* (2013.01); *H01J 2235/087* (2013.01); *H01J 2235/168* (2013.01); *H01J 2235/186* (2013.01)

(56) References Cited

U.S. PATENT DOCUMENTS

| | | | |
|---|---|---|---|
| 7,233,647 B2 * | 6/2007 | Turner | G21K 1/10 378/140 |
| 7,382,862 B2 * | 6/2008 | Bard | H01J 35/14 378/121 |
| 7,783,011 B2 * | 8/2010 | Ito | H01J 9/26 378/121 |
| 7,809,113 B2 | 10/2010 | Aoki et al. | |
| 7,873,146 B2 | 1/2011 | Okunuki et al. | |
| 2003/0021377 A1 * | 1/2003 | Turner | G01N 23/223 378/102 |
| 2004/0076260 A1 * | 4/2004 | Charles, Jr. | H01J 35/08 378/124 |
| 2004/0202282 A1 | 10/2004 | Miller | |
| 2005/0207537 A1 * | 9/2005 | Ukita | H01J 35/28 378/125 |
| 2007/0076849 A1 * | 4/2007 | Bard | H01J 35/14 378/121 |
| 2008/0112538 A1 | 5/2008 | Rogers | |
| 2011/0085641 A1 * | 4/2011 | Okunuki | H01J 35/065 378/62 |
| 2012/0140895 A1 * | 6/2012 | Okunuki | H01J 35/065 378/62 |
| 2014/0211919 A1 * | 7/2014 | Ogura | H01J 35/08 378/62 |
| 2014/0362972 A1 * | 12/2014 | Ogura | H01J 35/14 378/62 |
| 2014/0362973 A1 * | 12/2014 | Ogura | H01J 35/08 378/62 |
| 2014/0369469 A1 * | 12/2014 | Ogura | H01J 35/08 378/62 |
| 2015/0117616 A1 * | 4/2015 | Ishii | H01J 35/08 378/137 |

FOREIGN PATENT DOCUMENTS

| | | |
|---|---|---|
| JP | 2002343290 A | 11/2002 |
| JP | 2005327497 A | 11/2005 |
| JP | 2005346933 A | 12/2005 |
| JP | 2006523005 A | 10/2006 |
| JP | 2007207548 A | 8/2007 |
| JP | 2007265981 A | 10/2007 |
| WO | 2008/156361 A2 | 12/2008 |
| WO | 2011105035 A2 | 9/2011 |

* cited by examiner

X-RAY GENERATION APPARATUS AND X-RAY RADIOGRAPHIC APPARATUS

CROSS REFERENCE TO RELATED APPLICATIONS

This application is a U.S. National Stage of International application No. PCT/JP2012/072518 filed on Aug. 29, 2012 which claims priority from Japanese Patent Application JP 2011-189109 filed on Aug. 31, 2011, the disclosures of which is hereby incorporated by reference herein in their entirety.

TECHNICAL FIELD

The present invention relates to a transmission-type X-ray generation apparatus, which can be applied to, e.g., nondestructive X-ray radiography used in the fields of medical equipment and industrial equipment, and also relates to an X-ray radiographic apparatus employing the X-ray generation apparatus.

BACKGROUND ART

In an X-ray generation apparatus of transmission type generating an X-ray by colliding (bombarding) electrons against a transmission-type target, X-ray generation efficiency is generally very low. When electrons are accelerated to a high energy level and are collided against the transmission-type target to generate an X-ray, about 1% or less of energy of the colliding electrons is converted to the X-ray and the rest, i.e., about 99% or more of the energy, is converted to heat. It is also known that reflection electrons are produced upon electrons colliding against the transmission-type target, but the reflection electrons do not contribute to the generation of the X-ray. Therefore, an improvement of the X-ray generation efficiency is demanded.

PTL 1 discloses an X-ray tube in which the X-ray generation efficiency is increased by arranging, between an electron source and a target, an anode member having a conical channel with its aperture diameter gradually narrowing toward the target from the electron source, and by introducing electrons to impinge against the target after being subjected to elastic scattering at a channel surface.

CITATION LIST

Patent Literature

PTL 1 Japanese Patent Laid-Open No. 9-171788

SUMMARY OF INVENTION

Technical Problem

The above-mentioned related art provides a microfocus X-ray tube in which the number of electrons impinging against the target is substantially increased. However, the X-ray generation efficiency of the related-art X-ray tube is not sufficient in some cases when used in an X-ray radiographic apparatus.

Solution to Problem

According to the present invention, there is provided an X-ray generation apparatus of transmission type including an electron emission source, and a target generating an X-ray with collision of electrons emitted from the electron emission source against the target, wherein the X-ray generation apparatus further includes a secondary X-ray generation portion generating an X-ray with collision of electrons reflected by the target against the secondary X-ray generation portion, and the secondary X-ray generation portion and the target are arranged such that the X-ray generated with the direct collision of the electrons against the target and the X-ray generated with the collision of the electrons reflected by the target against the secondary X-ray generation portion are both radiated to an outside.

Advantageous Effects of Invention

With the present invention, in addition to the X-ray generated from the transmission-type target, the X-ray generated by the reflection electrons produced from the transmission-type target can also be efficiently taken out to the outside. As a result, the X-ray generation efficiency can be increased, and a transmission-type X-ray generation apparatus having a higher output adapted for X-ray radiography can be obtained.

DESCRIPTION OF EMBODIMENTS

First Embodiment

Figure 1A:
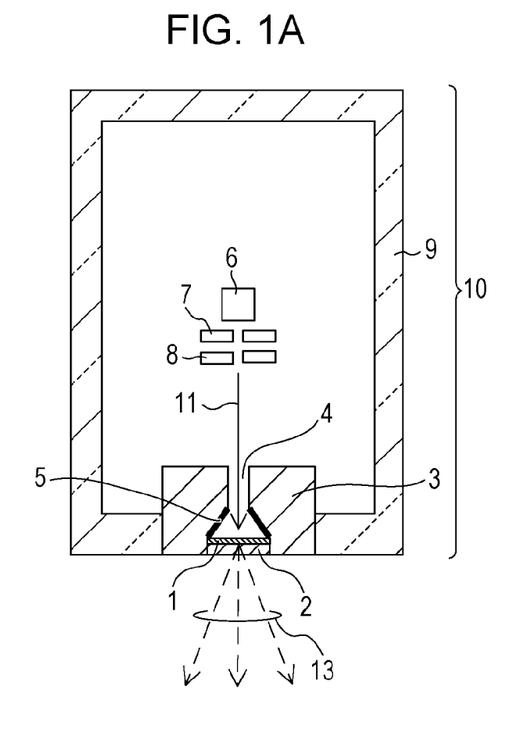
FIGS. 1A and 1B are schematic views of an X-ray tube used in the present invention.
Figure 1B:
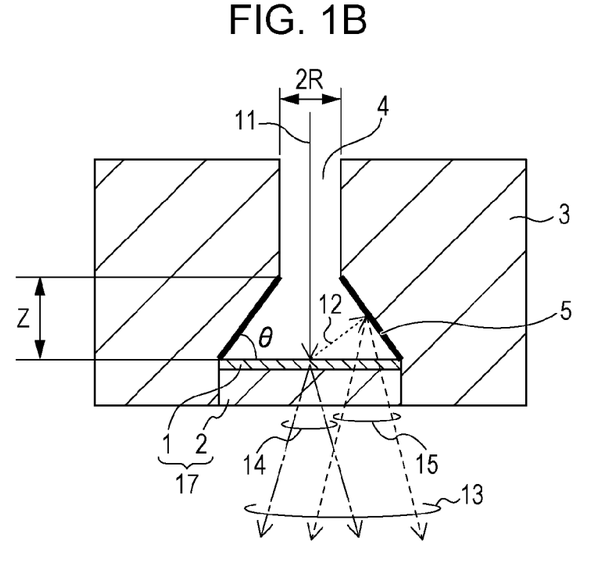

FIG. 1A is a schematic view of a transmission-type X-ray tube (hereinafter referred to as an "X-ray tube") 10 according to a first embodiment, and FIG. 1B is an enlarged view of a transmission-type target (hereinafter referred to as a "target") 1 and thereabout in FIG. 1A.

Referring to FIGS. 1A and 1B, the X-ray tube 10 includes an electron emission source 6, the target 1, a target support base (hereinafter referred to as a "support base") 2, an electron passage forming member 3, an electron passage 4, a secondary X-ray generation portion 5, and a vacuum vessel 9.

The vacuum vessel 9 is to keep the inside of the X-ray tube 10 under vacuum and is made of, e.g., glass or ceramic materials. A degree of vacuum within the vacuum vessel 9 may be about $10^{-4}$ to $10^{-8}$ Pa. The vacuum vessel 9 has an opening, and an electron passage forming member 3 including the electron passage 4 formed therein is joined to the opening. A support base 2 is joined to an inner wall surface of the electron passage 4, whereby the vacuum vessel 9 is enclosed. Further, an evacuation pipe (not illustrated) may be mounted to the vacuum vessel 9. When the evacuation pipe is mounted, a vacuum can be created inside the vacuum vessel 9, for example, by evacuating the vacuum vessel 9 into a vacuum state through the evacuation pipe and then sealing off a part of the evacuation pipe. A getter (not illustrated) may be disposed within the vacuum vessel 9 to keep the vacuum.

The electron emission source 6 is disposed within the vacuum vessel 9 in opposed relation to the target 1. The electron emission source 6 can be made of, e.g., a hot cathode, such as a tungsten filament or an impregnated cathode, or a cold cathode, such as a carbon nanotube. Electrons 11 emitted from the electron emission source 6 enter the electron passage 4, which is formed in the electron passage forming member 3, from one end thereof. After passing through the electron passage 4, the electrons 11 collide (bombard) against the target 1 that is disposed on the other end side of the electron passage 4, whereby an X-ray 13 is generated. The X-ray tube 10 may include an extraction electrode 7 and a lens electrode 8. In such a case, electrons are expelled out from the electron emission source 6 by the action of an electric field formed by the extraction electrode 7, and the extracted electrons are focused by the lens electrode 8 so as to impinge against the target 1. A voltage Va applied between the electron emission source 6 and the target 1 at that time is about 40 kV to 150 kV though depending on uses of the X-ray.

The structure of a portion of the X-ray tube 10, including the target 1 and thereabout, and the generation of the X-ray in the first embodiment will be described below with reference to FIG. 1B.

The target 1 is disposed on a surface of the support base 2 on the side colder to the electron emission source 6. The electron passage forming member 3 is disposed between the target 1 and the electron emission source 6. The electron passage forming member 3 includes the electron passage 4 in such a state that the electron passage 4 is surrounded by the electron passage forming member 3 and is opened at both ends thereof. In this embodiment, a cross-sectional area of the electron passage 4 at least in its end region on the side closer to the target 1 is larger than that in its end region on the side farther away from the target 1, and the cross-sectional area in the end region on the side closer to the target 1 is continuously increased. Further, the inner wall surface of the electron passage 4 in the region where the cross-sectional area is increased serves as the secondary X-ray generation portion 5. Because the secondary X-ray generation portion 5 is of the planar form in this embodiment, it may be called the "secondary X-ray generation surface 5" in some cases. It is just required that at least a part of the inner wall surface of the electron passage 4 in the region where the cross-sectional area is increased serves as the secondary X-ray generation portion (surface) 5. The secondary X-ray generation portion 5 may be formed as a part of the inner wall surface of the electron passage 4, or may be formed in the electron passage 4 by using a separate member from the electron passage forming member 3 that defines the electron passage 4.

In the X-ray tube 10 thus constructed, the electrons 11 expelled out from the electron emission source 6 collide against the target 1 after passing through the electron passage 4. With the collision of the electrons 11 accelerated to several tens kV to several hundreds kV against the target 1, an X-ray 14 is generated. The X-ray 14 generated at that time transmits through the support base 2 and is radiated to the outside of the X-ray tube 10. Further, when the electrons 11 collide against the target 1, reflection electrons 12 are generated in addition to the generation of the X-ray 14. Because the target 1 is made of a metal having a large atomic number as described later, reflectivity of electrons at the target 1 is comparatively large, i.e., several tens %. The reflection electrons 12 produced from the target 1 collide against the secondary X-ray generation portion 5, thereby generating an X-ray 15. The X-ray 15 (hereinafter referred to as the "secondary X-ray" in some cases) generated at that time is also radiated to the outside of the X-ray tube 10 after transmitting through the support base 2. Thus, at least a part of the X-ray 15 generated upon the reflection electrons 12 colliding against the secondary X-ray generation portion 5 is also radiated to the outside of the X-ray tube 10 after transmitting through a region of the target 1 against which the electrons collide, and further through the support base 2. In addition, a collimator for restricting an X-ray irradiation field may be disposed outside the X-ray tube 10.

Figure 2A:
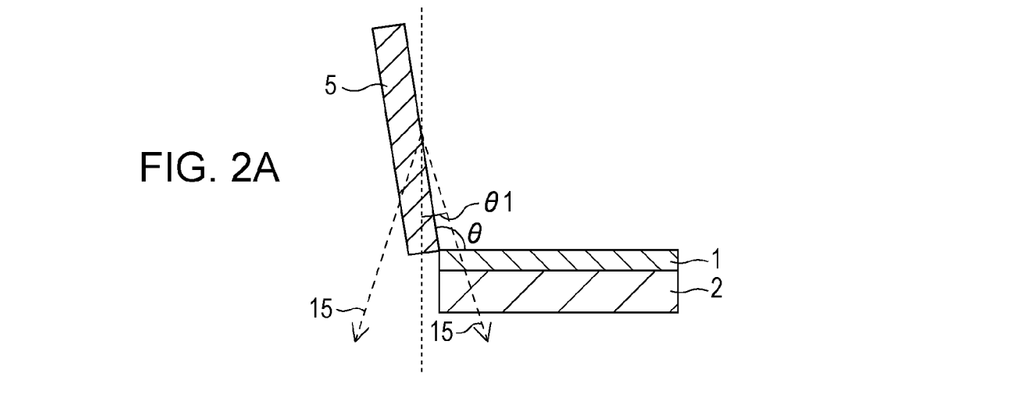
FIGS. 2A to 2C are schematic views illustrating the relationship between an angle $\theta$ formed by a secondary X-ray generation surface (portion) and a transmission-type target unit and a radiation direction of an X-ray.
Figure 2B:
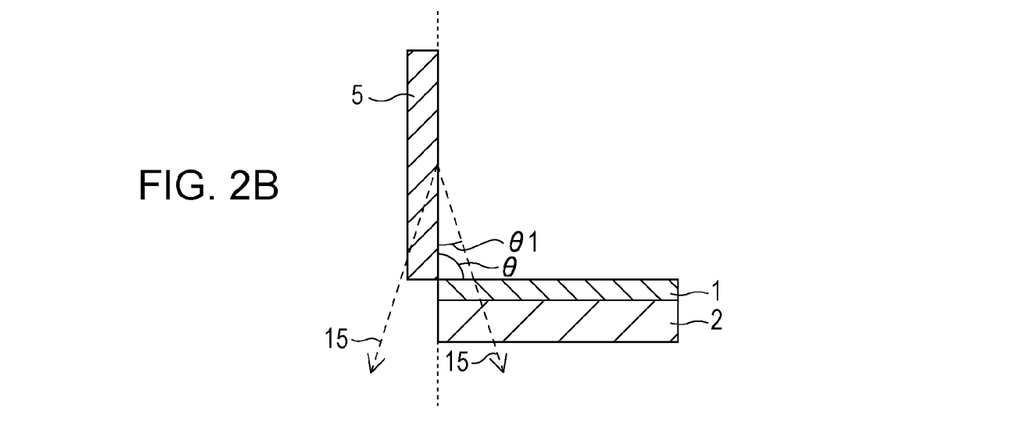
Figure 2C:
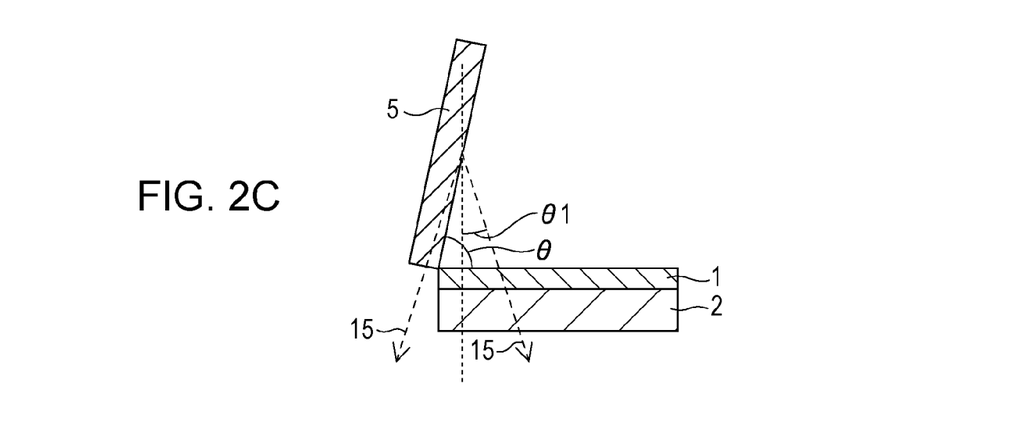

A desired shape of the electron passage 4 in this embodiment will be described below with reference to FIGS. 2A to 2C and FIGS. 3A and 3B. A preferable range of an angle θ, in FIG. 1B, formed by the secondary X-ray generation portion 5 and the target 1 is discussed here. FIGS. 2A to 2C illustrate the X-ray 15 generated from the secondary X-ray generation portion 5 upon the reflection electrons 12 colliding against the secondary X-ray generation portion 5. More specifically, FIGS. 2A to 2C illustrate the positional relationship between the X-ray 15, which is taken out at an arbitrary spreading angle θ1, for example, with respect to a line perpendicular to the target 1, and the surrounding members. FIG. 2A represents the case of θ>90°, FIG. 2B represents the case of θ=90°, and FIG. 2C represents the case of θ<90°. In the case of θ>90° in FIG. 2A, a large part of the generated X-ray 15 is absorbed in the secondary X-ray generation portion 5 while passing therethrough, whereas only a small part of the generated X-ray 15 is radiated to the outside. In the case of θ=90° in FIG. 2B, about a half of the generated X-ray 15 is absorbed in the secondary X-ray generation portion 5. In the case of θ<90° in FIG. 2C, a large part (at least a half or more) of the generated X-ray 15 is not absorbed in the secondary X-ray generation portion 5 and is radiated to the outside. Thus, by satisfying θ<90°, i.e., by forming the electron passage 4 in such a shape that the cross-sectional area of the electron passage 4 at its end on the side closer to the target 1 is larger than that at its end on the side farther away from the target 1, a rate at which the generated X-ray 15 is absorbed in the secondary X-ray generation portion 5 can be reduced and the X-ray 15 can be taken out in a larger amount.

Figure 3A:
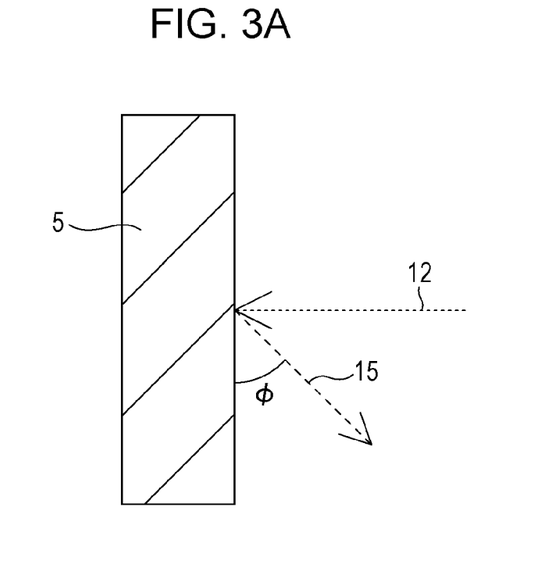
FIGS. 3A and 3B are explanatory views to explain dependency of X-ray intensity on an emergent angle.
Figure 3B:
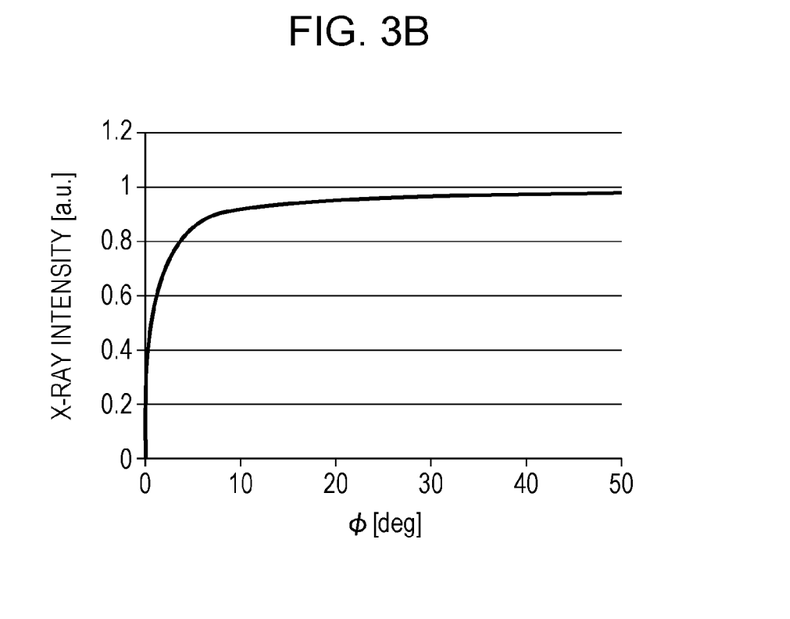

Furthermore, the preferable range of the angle θ can be set in consideration of dependency of the X-ray intensity on an emergent angle. FIGS. 3A and 3B are explanatory views to explain the dependency of X-ray intensity on an emergent angle. FIG. 3A illustrates a state where the reflection electrons 12 impinge against the secondary X-ray generation portion 5 and the generated X-ray 15 emerges at an emergent angle φ. FIG. 3B represents the relationship between the emergent angle φ of the X-ray in FIG. 3A and the X-ray intensity. Generally, because electrons accelerated to 10 kV to 200 kV penetrate into the secondary X-ray generation portion 5 about several microns without strongly depending on an incident angle, most of the X-ray is also generated in a zone that is positioned several microns inward of the surface of the secondary X-ray generation portion 5. The generated X-ray is radiated at various angles. The smaller the emergent angle φ of the X-ray in FIG. 3A, the longer is a distance through which the generated X-ray passes in the secondary X-ray generation portion 5. Therefore, in the case of φ<5°, for example, the X-ray intensity is abruptly reduced as the emergent angle φ decreases, as seen from FIG. 3B. Thus, given that a lower limit of the emergent angle is defined as $φ_0$ in consideration of the dependency of the X-ray intensity on the emergent angle, a more preferable range of the angle θ is provided by θ<90−$φ_0$, taking into account the above-mentioned preferable range together. When $φ_0$ is set to 5° from the relationship of FIG. 3B, θ<85° is obtained. In addition, considering a lower limit value of the angle θ from the viewpoint of efficiently colliding the electrons, reflected by the target 1, against the inner wall surface of the electron passage 4, the lower limit value of the angle θ is 10°, i.e., 10°<θ. Hence, an even more preferable range of the angle θ is 10°<θ<85°.

Figure 4A:
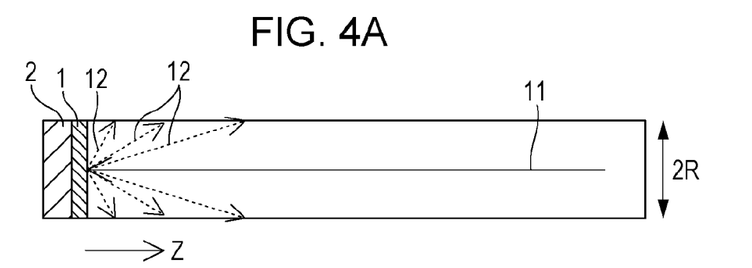
FIGS. 4A to 4C are explanatory views to explain a collision density distribution of reflection electrons.
Figure 4B:
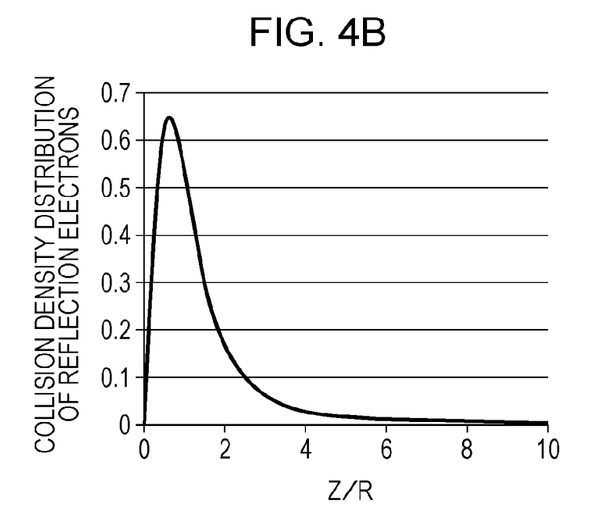
Figure 4C:
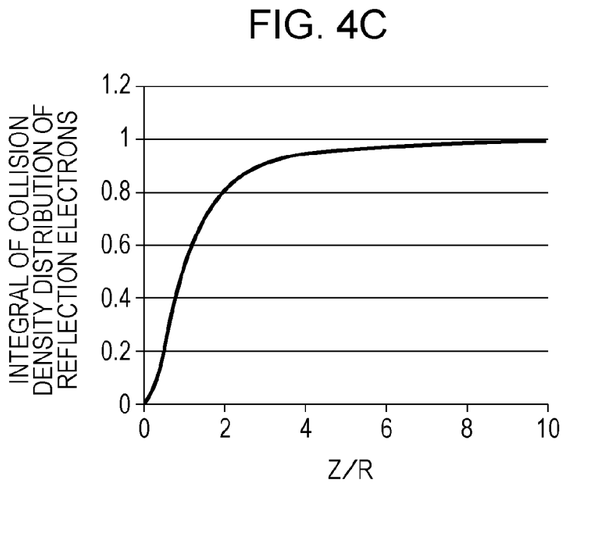

A preferable range of region where the secondary X-ray generation portion 5 is to be formed will be described below with reference to FIGS. 4A to 4C. The following description is made about a preferable range of a distance Z between the target 1 and an end of the secondary X-ray generation portion 5 on the side farther away from the target 1 (i.e., a distance Z over which the secondary X-ray generation portion 5 is formed) (see also FIG. 1B). The preferable range of the distance Z can be set in consideration of an arrival density distribution that represents a density at which the reflection electrons 12 produced from the target 1 arrive at peripheral regions. FIGS. 4A to 4C are explanatory views to explain the collision density distribution of the reflection electrons. FIG. 4A illustrates a model used in calculation, FIG. 4B is a graph representing the collision density distribution of the reflection electrons 12 produced by the incident electrons 11, and FIG. 4C is a graph representing an integral of the collision density distribution of the reflection electrons 12. Given that an opening width of the electron passage 4 (i.e., the electron passage forming member 3) perpendicular to a z-axis in FIG. 4A is denoted by 2R, many arrival points of the reflection electrons 12 produced from the target 1 are present on the surface of a peripheral region where a distance (a coordinate) z from the target 1 is not larger than 2R, and about 80% of all the reflection electrons 12 exist in that peripheral region. Further, about 95% of all the reflection electrons 12 exist in a peripheral region where the distance z is not larger than 4R. Accordingly, when the opening width of the electron passage 4 is defined as 2R, the secondary X-ray generation portion 5 is formed at least in the region where the distance z is not larger than 2R, and more particularly in the region where the distance z is not larger than 4R. Moreover, when the distance z reaches 20R, the collision density of the reflection electrons converges to substantially zero. Thus, the opening width 2R of the electron passage forming member 3 and the distance (size) Z over which the secondary X-ray generation portion 5 is formed preferably satisfy the relationship of (2R≤Z≤20R). It is more preferable to satisfy the relationship of (4R≤Z≤20R).

While, in FIG. 1B, the secondary X-ray generation portion 5 is formed over the entire inner wall surface of the electron passage 4 in its region where the cross-sectional area of the electron passage 4 is increased, the secondary X-ray generation portion 5 is not always required to be formed over the entire inner wall surface of the electron passage 4 in its region where the cross-sectional area of the electron passage 4 is increased. In other words, the secondary X-ray generation portion 5 is just required to be formed at least in a region of the electron passage 4, which region includes the above-mentioned range of the distance Z.

To provide the structure for generating the secondary X-ray by colliding the reflection electrons 12 against the secondary X-ray generation portion 5 in the electron passage 4 and for taking the generated secondary X-ray to the outside of the X-ray tube 10, the secondary X-ray generation portion 5 and the target 1 may be arranged in this embodiment as follows. In one example, the secondary X-ray generation portion 5 is arranged such that it protrudes to cover above the surface of the target 1 against which the electrons collide. In another example, the secondary X-ray generation portion 5 and the target 1 are arranged such that the X-ray generated upon the electrons directly colliding against the target 1 and the secondary X-ray can be both radiated to the outside (in superimposed relation). In such a case, the target 1 can be made of a material that reflects 20% to 60% of the colliding electrons. In the above-mentioned examples, as in the foregoing embodiment, the secondary X-ray generation portion 5 may be formed as a part of the inner wall surface of the electron passage 4, or may be formed in the electron passage 4 by using a separate member from the electron passage forming member 3 that defines the electron passage 4.

The secondary X-ray generation portion 5 may be formed in a configuration capable of increasing an amount of the X-ray that is generated upon the reflection electrons 12 colliding against the secondary X-ray generation portion 5 and that transmits through the region of the target 1 against which the electrons collide.

The target 1 can be made of a material having a high melting point and high X-ray generation efficiency. A metal having an atomic number of 26 or more is suitable as such a material. For example, tungsten, tantalum, molybdenum, etc. may be used. A thickness of the target 1 is preferably several μm to several tens μm from the viewpoint of reducing absorption of the generated X-ray while the generated X-ray transmits through the target 1.

The support base 2 can be made of a material having strength sufficient to support the target 1 and absorbing both the X-rays generated from the target 1 and the secondary X-ray generation portion 5 in a less amount. Further, the support base 2 may be made of a material having a high thermal conductivity such that heat generated from the target 1 can be quickly dissipated. For example, diamond, silicon nitride, aluminum nitride, etc. may be used. An appropriate thickness of the support base 2 is about 0.1 mm to several mm.

The secondary X-ray generation portion 5 can be made of a material having a high melting point and high X-ray generation efficiency. A metal having an atomic number of 26 or more is suitable as such a material. For example, tungsten, tantalum, molybdenum, etc. may be used. A thickness of the secondary X-ray generation portion 5 may be not smaller than an electron penetration length. In practice, the thickness of the secondary X-ray generation portion 5 is preferably several μm or more.

The material of the electron passage forming member 3 may be the same as that of the secondary X-ray generation portion 5. In such a case, a surface portion of the electron passage forming member 3 serves as the secondary X-ray generation portion 5. Alternatively, the material of the electron passage forming member 3 may be different from that of the secondary X-ray generation portion 5. Moreover, the material of the electron passage forming member 3 may have a high thermal conductivity such that heat generated in the secondary X-ray generation portion 5 can be quickly dissipated. For example, tungsten, tantalum, molybdenum, copper, silver, gold, nickel, etc. may be used.

Second Embodiment

A second embodiment differs from the first embodiment in shapes of the electron passage forming member 3 and the electron passage 4. Other common points than the shapes of the electron passage forming member 3 and the electron passage 4 are similar to those in the first embodiment.

Figure 5A:
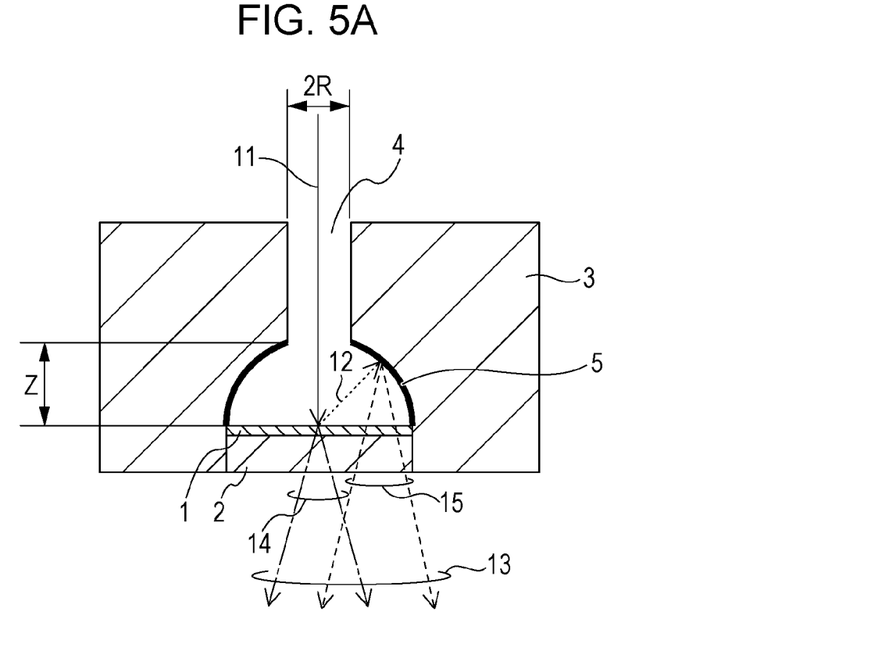
FIGS. 5A and 5B are schematic views illustrating other examples of the X-ray tube used in the present invention.

FIG. 5A is an enlarged view of the target 1 and thereabout in the second embodiment. The electron passage 4 opened at both ends thereof is formed in the electron passage forming member 3 surrounding the electron passage 4. A cross-sectional area of the electron passage 4 at least in its end region on the side closer to the target 1 is larger than that in its end region on the side farther away from the target 1, and the cross-sectional area in the end region on the side closer to the target 1 is continuously increased. Further, as illustrated in FIG. 5A, a cross-section of the electron passage 4 in a direction perpendicular to the target 1 has a circular arc shape that is convex upward when the side closer to the target 1 is defined as the downward side. Moreover, the inner wall surface of the electron passage 4 in the region where the cross-sectional area is increased serves as the secondary X-ray generation portion 5. It is just required that at least a part of the inner wall surface of the electron passage 4 in the region where the cross-sectional area is increased serves as the secondary X-ray generation portion 5. The secondary X-ray generation portion 5 may be formed as a part of the inner wall surface of the electron passage 4, or may be formed in the electron passage 4 by using a separate member from the electron passage forming member 3 that defines the electron passage 4.

In the construction described above, the electrons 11 expelled out from the electron emission source 6 collide against the target 1 after passing through the electron passage 4, whereby an X-ray 14 is generated. The X-ray 14 generated at that time transmits through the support base 2 and is radiated to the outside of the X-ray tube 10. Further, the reflection electrons 12 produced upon the electrons 11 colliding against the target 1 generate an X-ray 15 upon colliding against the secondary X-ray generation portion 5. The X-ray 15 generated at that time is also radiated to the outside of the X-ray tube 10 after transmitting through the support base 2.

In the second embodiment, since the cross-section of the secondary X-ray generation portion 5 has a circular arc shape that is convex upward when the side closer to the target 1 is defined as the downward side, a rate at which the X-ray 15 generated from the secondary X-ray generation portion 5 is absorbed in the secondary X-ray generation portion 5 is reduced, and the X-ray 15 can be taken out in a larger amount.

A preferable range of the region where the secondary X-ray generation portion 5 is formed is similar to that in the first embodiment. More specifically, given that the opening width of the electron passage 4 (i.e., the electron passage forming member 3) is defined as 2R, the secondary X-ray generation portion 5 can be formed in a region of the electron passage 4 where the above-mentioned distance Z is not larger than 4R or at least not larger than 2R. Further, the opening width 2R of the electron passage forming member 3 and the distance Z over which the secondary X-ray generation portion 5 is formed preferably satisfy the relationship of ($2R \leq Z \leq 20R$). It is more preferable to satisfy the relationship of ($4R \leq Z \leq 20R$).

Moreover, the secondary X-ray generation portion 5 and the target 1 may be arranged such that the secondary X-ray generation portion 5 having the cross-section in the upwardly convex circular-arc shape protrudes to cover above the surface of the target 1 against which the electrons collide. In another example, the secondary X-ray generation portion 5 having the cross-section in the upwardly convex circular-arc shape and the target 1 may be arranged such that the X-ray generated upon the electrons directly colliding against the target 1 and the secondary X-ray are both radiated to the outside (in superimposed relation). In such a case, the target 1 can be made of a material that reflects 20% to 60% of the colliding electrons. In the above-mentioned examples, as in the foregoing embodiment, the secondary X-ray generation portion 5 may be formed as a part of the inner wall surface of the electron passage 4, or may be formed in the electron passage 4 by using a separate member from the electron passage forming member 3 that defines the electron passage 4.

The secondary X-ray generation portion 5 may be formed in a configuration capable of increasing an amount of the X-ray that is generated upon the reflection electrons 12 colliding against the secondary X-ray generation portion 5 and that transmits through the region of the target 1 against which the electrons collide.

Third Embodiment

A third embodiment differs from the first embodiment in shapes of the electron passage forming member 3 and the electron passage 4. Other common points than the shapes of the electron passage forming member 3 and the electron passage 4 are similar to those in the first embodiment.

Figure 5B:
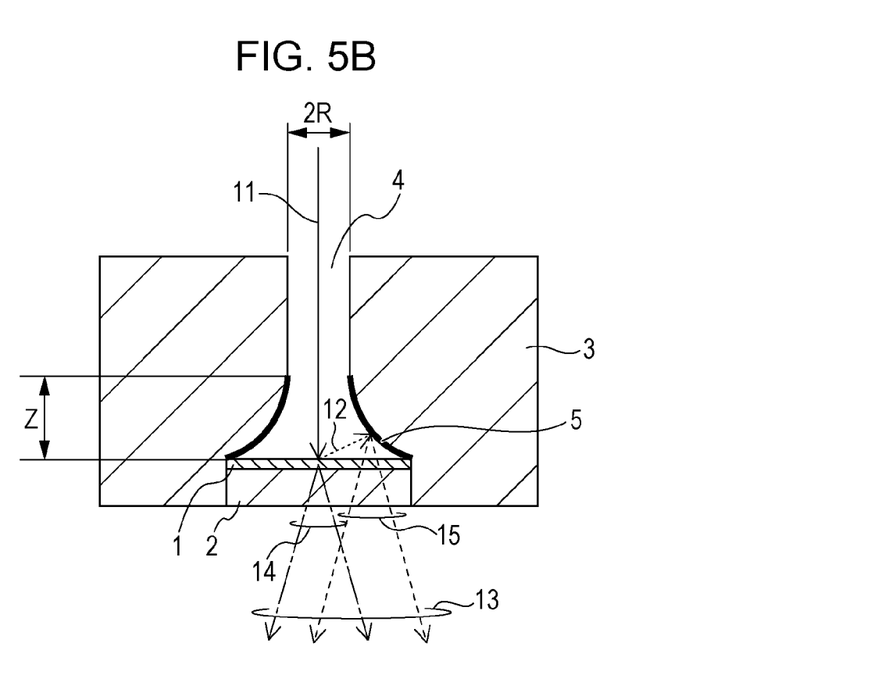

FIG. 5B is an enlarged view of the target 1 and thereabout in the third embodiment. The electron passage 4 opened at both ends thereof is formed in the electron passage forming member 3 surrounding the electron passage 4. A cross-sectional area of the electron passage 4 at least in its end region on the side closer to the target 1 is larger than that in its end region on the side farther away from the target 1, and the cross-sectional area in the end region on the side closer to the target 1 is continuously increased. Further, as illustrated in FIG. 5B, a cross-section of the electron passage 4 in a direction perpendicular to the target 1 has a circular arc shape that is convex downward when the side closer to the target 1 is defined as the downward side. Moreover, the inner wall surface of the electron passage 4 in the region where the cross-sectional area is increased serves as the secondary X-ray generation portion 5. It is just required that at least a part of the inner wall surface of the electron passage 4 in the region where the cross-sectional area is increased serves as the secondary X-ray generation portion 5. The secondary X-ray generation portion 5 may be formed as a part of the inner wall surface of the electron passage 4, or may be formed in the electron passage 4 by using a separate member from the electron passage forming member 3 that defines the electron passage 4.

In the construction described above, the electrons 11 expelled out from the electron emission source 6 collide against the target 1 after passing through the electron passage 4, whereby an X-ray 14 is generated. The X-ray 14 generated at that time transmits through the support base 2 and is radiated to the outside of the X-ray tube 10. Further, the reflection electrons 12 produced upon the electrons 11 colliding against the target 1 generate an X-ray 15 upon colliding against the secondary X-ray generation portion 5. The X-ray 15 generated at that time is also radiated to the outside of the X-ray tube 10 after transmitting through the support base 2.

In the third embodiment, since the cross-section of the secondary X-ray generation portion 5 has a circular arc shape that is convex downward when the side closer to the target 1 is defined as the downward side, a rate at which the X-ray 15 generated from the secondary X-ray generation portion 5 is absorbed in the secondary X-ray generation portion 5 is reduced, and the X-ray 15 can be taken out in a larger amount.

A preferable range of the region where the secondary X-ray generation portion 5 is formed is similar to that in the first embodiment. More specifically, given that the opening width of the electron passage 4 (i.e., the electron passage forming member 3) is defined as 2R, the secondary X-ray generation portion 5 can be formed in a region of the electron passage 4 where the above-mentioned distance Z is not larger than 4R or at least not larger than 2R. Further, the opening width 2R of the electron passage forming member 3 and the distance Z over which the secondary X-ray generation portion 5 is formed preferably satisfy the relationship of ($2R \leq Z \leq 20R$). It is more preferable to satisfy the relationship of ($4R \leq Z \leq 20R$).

Moreover, the secondary X-ray generation portion 5 and the target 1 may be arranged such that the secondary X-ray generation portion 5 having the cross-section in the downwardly convex circular-arc shape protrudes to cover above the surface of the target 1 against which the electrons collide. In another example, the secondary X-ray generation portion 5 having the cross-section in the downwardly convex circular-arc shape and the target 1 may be arranged such that the X-ray generated upon the electrons directly colliding against the target 1 and the secondary X-ray are taken out to the outside in superimposed relation. In such a case, the target 1 can be made of a material that reflects 20% to 60% of the colliding electrons. In the above-mentioned examples, as in the foregoing embodiments, the secondary X-ray generation portion 5 may be formed as a part of the inner wall surface of the electron passage 4, or may be formed in the electron passage 4 by using a separate member from the electron passage forming member 3 that defines the electron passage 4.

The secondary X-ray generation portion 5 may be formed in a configuration capable of increasing an amount of the X-ray that is generated upon the reflection electrons colliding against the secondary X-ray generation portion 5 and that transmits through the region of the target 1 against which the electrons collide.

Fourth Embodiment

A fourth embodiment differs from the first embodiment in shapes of the electron passage forming member 3 and the electron passage 4. Other common points than the shapes of the electron passage forming member 3 and the electron passage 4 are similar to those in the first embodiment.

Figure 6A:
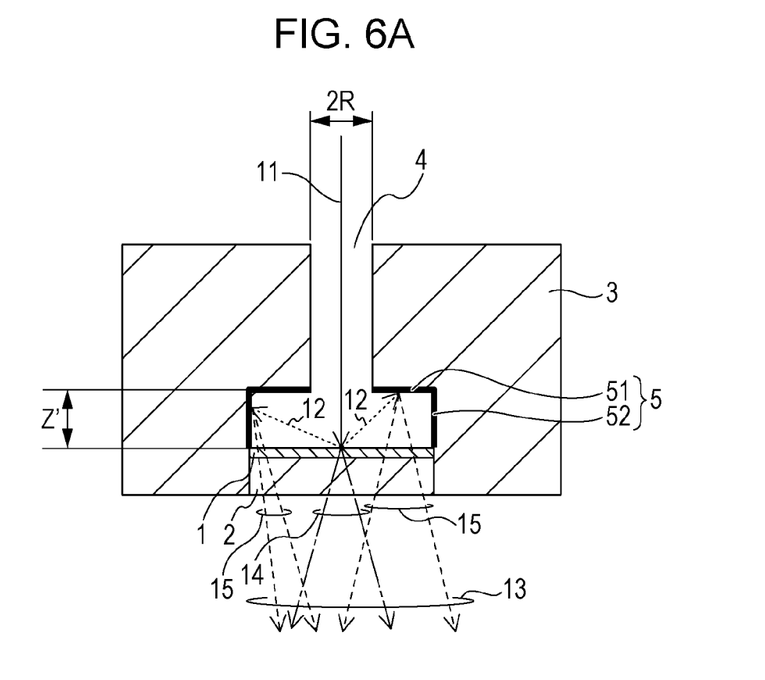
FIGS. 6A and 6B are schematic views illustrating still other examples of the X-ray tube used in the present invention.

FIG. 6A is an enlarged view of the target 1 and thereabout in the fourth embodiment. The electron passage 4 opened at both ends thereof is formed in the electron passage forming member 3 surrounding the electron passage 4. A cross-sectional area of the electron passage 4 at least in its end region on the side closer to the target 1 is larger than that in its end region on the side farther away from the target 1, and the cross-sectional area in the end region on the side closer to the target 1 is increased with a change in one step. Further, the inner wall surface of the electron passage 4 in the region where the cross-sectional area is increased serves as the secondary X-ray generation portion 5. It is just required that at least a part of the inner wall surface of the electron passage 4 in the region where the cross-sectional area is increased serves as the secondary X-ray generation portion 5. The secondary X-ray generation portion 5 is made up of a secondary X-ray generation portion 51 extending horizontally parallel to the target 1, and a secondary X-ray generation portion 52 extending perpendicularly to the target 1. The secondary X-ray generation portion 51 may be not parallel to the target 1, and the secondary X-ray generation portion 52 may be not perpendicular to the target 1. An angle formed by the secondary X-ray generation portion 51 and 52 may be not 90°. The secondary X-ray generation portion 5 may be formed as a part of the inner wall surface of the electron passage 4, or may be formed in the electron passage 4 by using a separate member from the electron passage forming member 3 that defines the electron passage 4.

In the construction described above, the electrons 11 expelled out from the electron emission source 6 collide against the target 1 after passing through the electron passage 4, whereby an X-ray 14 is generated. The X-ray 14 generated at that time transmits through the support base 2 and is radiated to the outside of the X-ray tube 10. Further, a part of the reflection electrons 12 produced upon the electrons 11 colliding against the target 1 generates an X-ray 15 upon colliding against the secondary X-ray generation portion 51, and another part of the reflection electrons 12 generates another X-ray 15 upon colliding against the secondary X-ray generation portion 52. Both the X-rays 15 generated from the secondary X-ray generation portions 51 and 52 are also radiated to the outside of the X-ray tube 10 after transmitting through the support base 2.

In the fourth embodiment, since the secondary X-ray generation portion 51 is formed horizontally parallel to the target 1, a rate at which the X-ray 15 generated from the secondary X-ray generation portion 51 is absorbed in the secondary X-ray generation portion 51 is reduced, and the X-ray 15 can be taken out in a larger amount.

A preferable range of the region where the secondary X-ray generation portion 5 is formed in the fourth embodiment is described below. As discussed above with reference to FIGS. 4A to 4C, the collision density of the reflection electrons is maximized near (Z<1R) the target 1. Therefore, the secondary X-ray generation portion 51 is formed at a position relatively near the target 1. On the other hand, the secondary X-ray generation portion 52 also contributes to the generation of the X-ray. Thus, a distance Z' over which the secondary X-ray generation portion 52 is formed can be set such that a total amount of the X-rays generated from both the secondary X-ray generation portions 51 and 52 is maximized.

Moreover, the secondary X-ray generation portion 5 and the target 1 may be arranged such that the secondary X-ray generation portions 51 and 52 protrude to cover above the surface of the target 1 against which the electrons collide. In another example, the secondary X-ray generation portions 51 and 52 and the target 1 may be arranged such that the X-ray generated upon the electrons directly colliding against the target 1 and the secondary X-rays are all radiated to the outside (in superimposed relation). In such a case, the target 1 can be made of a material that reflects 20% to 60% of the colliding electrons. In the above-mentioned examples, as in the foregoing embodiments, the secondary X-ray generation portion 5 may be formed as a part of the inner wall surface of the electron passage 4, or may be formed in the electron passage 4 by using a separate member from the electron passage forming member 3 that defines the electron passage 4.

The secondary X-ray generation portion 5 may be formed in a configuration capable of increasing an amount of the X-ray that is generated upon the reflection electrons colliding against the secondary X-ray generation portion 5 and that transmits through the region of the target 1 against which the electrons collide.

Fifth Embodiment

A fifth embodiment differs from the fourth embodiment in parts of the shapes of the electron passage forming member 3 and the electron passage 4. Other common points than the shapes of the electron passage forming member 3 and the electron passage 4 are similar to those in the fifth embodiment.

Figure 6B:
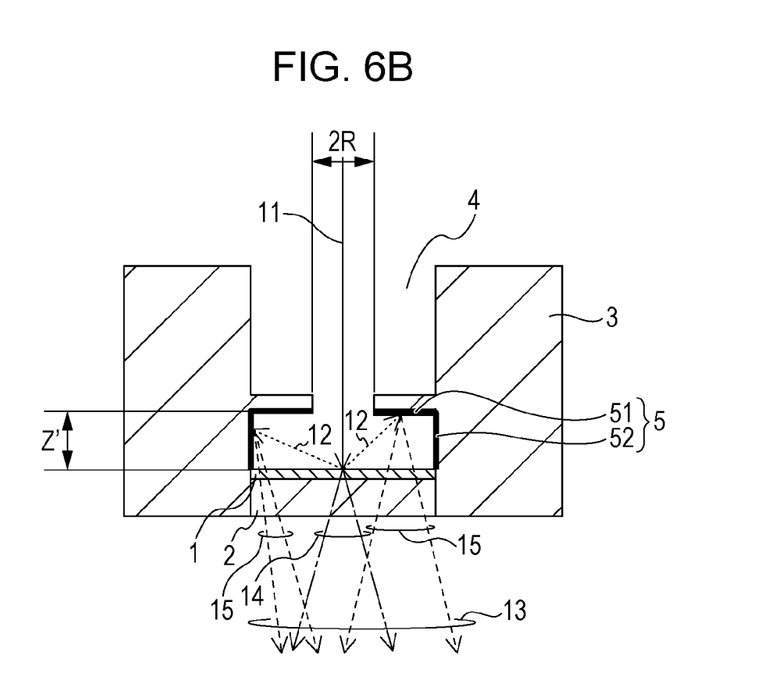

FIG. 6B is an enlarged view of the target 1 and thereabout in the fifth embodiment. The electron passage 4 opened at both ends thereof is formed in the electron passage forming member 3 surrounding the electron passage 4. Midway the electron passage 4, there is a portion partly projecting from the inner wall surface of the electron passage 4 (that portion being referred to as a "projection" hereinafter). The projection can be provided in an annular shape when viewed from the side closer to the target 1. The projection may be formed by the same material as that of the electron passage forming member 3 that defines the electron passage 4, or may be formed by using a separate member from the electron passage forming member 3 that defines the electron passage 4. A region of the inner wall surface of the electron passage 4 from its end region on the side closer to the target 1 to the projection serves as a secondary X-ray generation portion 52, and a surface region of the projection positioned to face the target 1 serves as a secondary X-ray generation portion 51. Thus, the secondary X-ray generation portion 5 is made up of the secondary X-ray generation portion 51 and the secondary X-ray generation portion 52. The secondary X-ray generation portion 51 may be not horizontal parallel to the target 1, and the secondary X-ray generation portion 52 may be not perpendicular to the target 1. An angle formed by the secondary X-ray generation portions 51 and 52 may be not 90°. The secondary X-ray generation portion 5 may be formed as a part of the inner wall surface of the electron passage 4, or may be formed in the electron passage 4 by using a separate member from the electron passage forming member 3 that defines the electron passage 4.

A preferable range of the region where the secondary X-ray generation portion 5 is formed is similar to that in the fourth embodiment. More specifically, the secondary X-ray generation portion 51 is formed at a position relatively near the target 1. On the other hand, the secondary X-ray generation portion 52 also contributes to the generation of the X-ray. Thus, a distance Z' over which the secondary X-ray generation portion 52 is formed can be set such that a total amount of the X-rays generated from both the secondary X-ray generation portions 51 and 52 is maximized.

Moreover, the secondary X-ray generation portion 5 and the target 1 may be arranged such that the secondary X-ray generation portions 51 and 52 protrude to cover above the surface of the target 1 against which the electrons collide. In another example, the secondary X-ray generation portions 51 and 52 and the target 1 may be arranged such that the X-ray generated upon the electrons directly colliding against the target 1 and the secondary X-rays are all radiated to the outside (in superimposed relation). In such a case, the target 1 can be made of a material that reflects 20% to 60% of the colliding electrons. In the above-mentioned examples, as in the foregoing embodiments, the secondary X-ray generation portion 5 may be formed as a part of the inner wall surface of the electron passage 4, or may be formed in the electron passage 4 by using a separate member from the electron passage forming member 3 that defines the electron passage 4.

In any of the embodiments described above, the X-ray 15 generated by the reflection electrons 12 produced from the target 1 is also efficiently taken out in addition to the X-ray 14 generated from the target 1. As a result, the X-ray generation efficiency can be increased.

Sixth Embodiment

Figure 7:
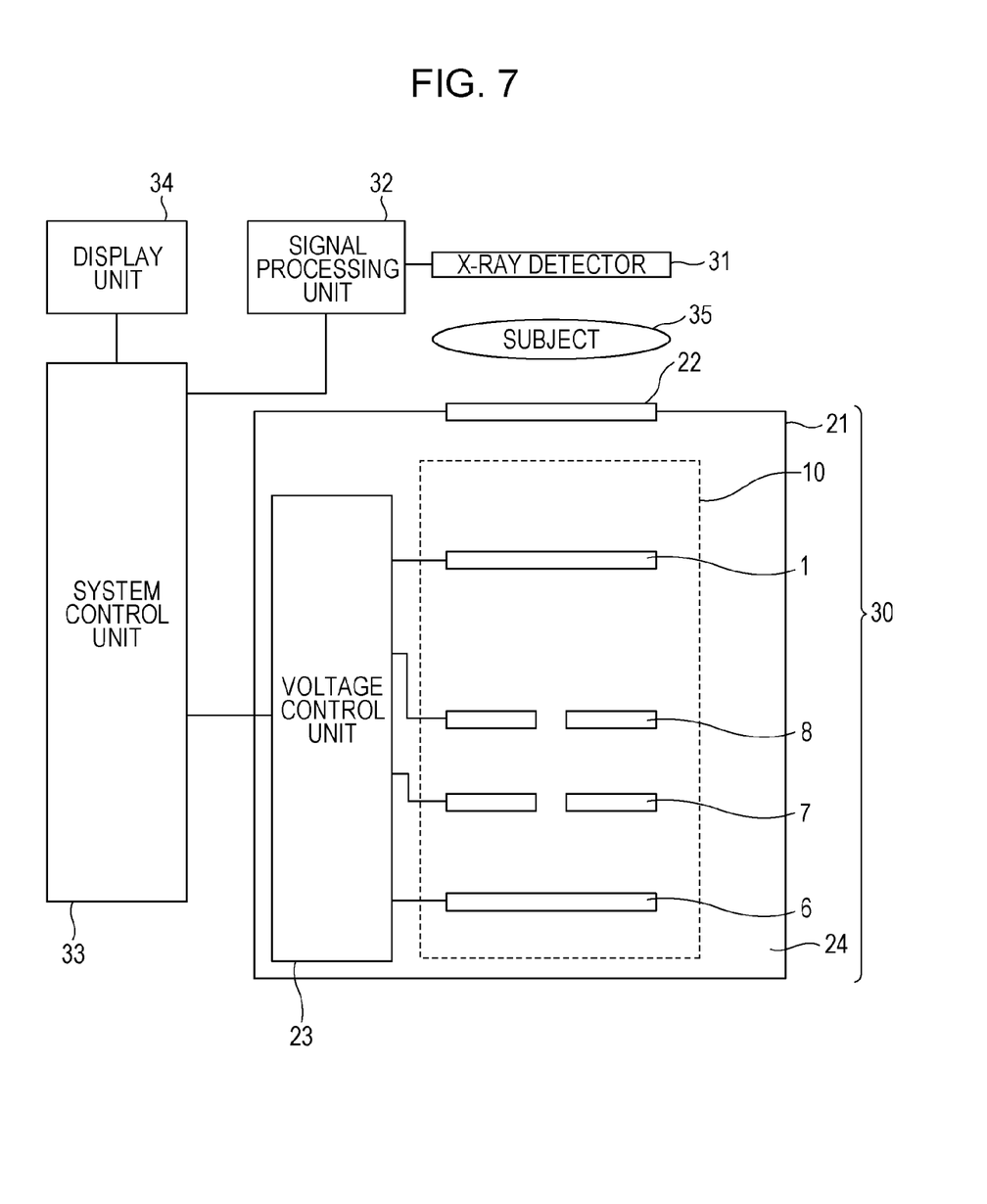
FIG. 7 is a block diagram of an X-ray radiographic apparatus including an X-ray generation apparatus according to the present invention.

FIG. 7 is a block diagram of an X-ray generation apparatus 30, which includes the X-ray tube 10 according to one of the first to fifth embodiments, and an X-ray radiographic apparatus employing the X-ray generation apparatus.

The X-ray generation apparatus 30, including the X-ray tube 10, according to the present invention is first described. In the X-ray generation apparatus 30, the X-ray tube 10 is disposed inside an envelope 21. The envelope 21 has an X-ray taking-out window 22. An X-ray emitted from the X-ray tube 10 transmits through the X-ray taking-out window 22, and it is radiated to the outside of the X-ray generation apparatus 30.

An insulating medium 24 may be filled in an inner empty space of the envelope 21 within which the X-ray tube 10 is disposed. One example of the insulating medium 24 is electrical insulating oil that serves as not only an insulating medium, but also a cooling medium to cool the X-ray tube 10. The electrical insulating oil can be provided as, e.g., mineral oil or silicone oil. Another example usable as the insulating medium 24 is a fluorine-based electrical insulating liquid.

A voltage control unit 23 made up of a circuit board, an insulating transformer, etc. (not illustrated) may be disposed inside the envelope 21. When the voltage control unit 23 is disposed, the generation of the X-ray can be controlled, for example, by applying a voltage signal to the X-ray tube 10 from the voltage control unit 23.

The X-ray radiographic apparatus employing the X-ray generation apparatus 30 is described below. The X-ray radiographic apparatus includes the X-ray generation apparatus 30, an X-ray detector 31, a signal processing unit 32, a system control unit (simply called a "control unit") 33, and a display unit 34. The X-ray detector 31 is connected to the control unit 33 via the signal processing unit 32, and the control unit 33 is connected to the display unit 34 and the voltage control unit 23.

Various processes executed in the X-ray generation apparatus 30 are controlled by the control unit 33 in a centralized manner. For example, the control unit 33 controls X-ray radiography that is performed by the X-ray generation apparatus 30 and the X-ray detector 31. An X-ray radiated from the X-ray generation apparatus 30 is detected by the X-ray detector 31 after transmitting through a subject (specimen) 35. An X-ray transmission image of the subject 35 is thus picked up. The picked-up X-ray transmission image is displayed on the display unit 34. Further, the control unit 33 controls the operation of the X-ray generation apparatus 30, for example, by controlling the voltage signal applied to the X-ray tube 10 through the voltage control unit 23.

According to the sixth embodiment, as described above, a transmission-type X-ray generation apparatus having higher X-ray generation efficiency is provided, and an X-ray radiographic apparatus having a smaller size and higher resolution is provided by employing that transmission-type X-ray generation apparatus.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-189109, filed Aug. 31, 2011, which is hereby incorporated by reference herein in its entirety.

REFERENCE SIGNS LIST

1: transmission-type target (target)
2: target support base
3: electron passage forming member
4: electron passage
5, 51, 52: secondary X-ray generation portions
6: electron emission source
7: extraction electrode
8: lens electrode
9: vacuum vessel
10: transmission-type X-ray tube
11: electron
12: reflection electron
13 to 15: X-rays
21: envelope
22: X-ray taking-out window
23: voltage control unit
24: insulating medium
30: X-ray generation apparatus
31: X-ray detector 32: signal processing unit
33: system control unit
34: display unit
35: subject (specimen)

The invention claimed is:

1. An X-ray generation apparatus of transmission type comprising:
   an electron emission source; and
   a target generating an X-ray with collision of electrons emitted from the electron emission source against the target,
   wherein the X-ray generation apparatus further comprises a secondary X-ray generation portion generating an X-ray with collision of electrons reflected by the target against the secondary X-ray generation portion, and
   the secondary X-ray generation portion and the target are arranged such that the X-ray generated with the direct collision of the electrons against the target and the X-ray generated with the collision of the electrons reflected by the target against the secondary X-ray generation portion are both radiated to an outside,
   an electron passage surrounded by and formed in an electron passage forming member, and positioned on one side of the target closer to the electron emission source,
   wherein the electrons emitted from the electron emission source collide against the target after passing through the electron passage,
   wherein a cross-sectional area of the electron passage at least at an end thereof on a side closer to the target is larger than a cross-sectional area of the electron passage on a side farther away from the target, and at least a part of an inner wall surface of a region of the electron passage where the cross-sectional area thereof is increased serves as the secondary X-ray generation portion, and
   wherein an opening size (2R) of the electron passage at the end thereof on the side farther away from the target and a distance (Z) from an end of the secondary X-ray generation portion on the side closer to the target to an end of the secondary X-ray generation portion on the side farther away from the target satisfy a following relationship of:

$2R \leq Z \leq 20R$.

2. The X-ray generation apparatus according to claim 1, wherein an angle θ formed by the secondary X-ray generation portion and the target satisfies a following relationship of:

$10° < \theta < 85°$.

3. The X-ray generation apparatus according to claim 1, wherein the cross-sectional area of the electron passage is increased toward at least the end thereof on the side closer to the target with a step-like change.

4. The X-ray generation apparatus according to claim 1, wherein the cross-sectional area of the electron passage is continuously increased toward at least the end thereof on the side closer to the target.

5. The X-ray generation apparatus according to claim 4, wherein the cross-sectional area of the electron passage is linearly increased toward at least the end thereof on the side closer to the target.

6. The X-ray generation apparatus according to claim 4, wherein the cross-sectional area of the electron passage is increased toward at least the end thereof on the side closer to the target such that a cross-section of the electron passage has an upwardly convex circular-arc shape.

7. The X-ray generation apparatus according to claim 4, wherein the cross-sectional area of the electron passage is increased toward at least the end thereof on the side closer to the target such that a cross-section of the electron passage has a downwardly convex circular-arc shape.

8. The X-ray generation apparatus according to claim 1, wherein at least a part of the X-ray generated upon the collision of the reflection electrons against the secondary X-ray generation portion transmits through a region of the target against which the electrons collide.

9. The X-ray generation apparatus according to claim 8, wherein the target is made of one of tungsten, tantalum and molybdenum.

10. The X-ray generation apparatus according to claim 8, wherein the secondary X-ray generation portion is made of one of tungsten, tantalum and molybdenum.

11. The X-ray generation apparatus according to claim 8, wherein the target is disposed on a surface of a support base, which surface is positioned to face the electron emission source.

12. The X-ray generation apparatus according to claim 11, wherein the support base is made of one of diamond, silicon nitride, and aluminum nitride.

13. The X-ray generation apparatus according to claim 1, wherein the electron emission source is disposed inside a vacuum vessel, and
   the electron passage forming member is disposed in an opening of the vacuum vessel.

14. The X-ray generation apparatus according to claim 13, wherein the vacuum vessel is disposed in an envelope, and an insulating medium is filled in an empty space between the vacuum vessel and the envelope.

15. The X-ray generation apparatus according to claim 14, wherein a voltage control unit configured to output a voltage signal for controlling the generation of the X-ray is disposed inside the envelope.

16. A radiography system comprising:
   the X-ray generation apparatus according to claim 1;
   an X-ray detector configured to detect an X-ray having been radiated from the X-ray generation apparatus and having transmitted through a subject; and
   a control unit configured to control the X-ray generation apparatus and the X-ray detector.

17. An X-ray generation apparatus of transmission type comprising:
   an electron emission source; and
   a target generating an X-ray with collision of electrons emitted from the electron emission source against the target,
   wherein the X-ray generation apparatus further comprises a secondary X-ray generation portion generating an X-ray with collision of electrons reflected by the target against the secondary X-ray generation portion, and
   the secondary X-ray generation portion and the target are arranged such that the X-ray generated with the direct collision of the electrons against the target and the X-ray generated with the collision of the electrons reflected by the target against the secondary X-ray generation portion are both radiated to an outside,
   an electron passage surrounded by and formed in an electron passage forming member, and positioned on one side of the target closer to the electron emission source,
   wherein the electrons emitted from the electron emission source collide against the target after passing through the electron passage, wherein a cross-sectional area of the electron passage at least at an end thereof on a side closer to the target is larger than a cross-sectional area of the electron passage on a side farther away from the target, and at least a part of an inner wall surface of a region of the electron passage where the cross-sectional area thereof is increased serves as the secondary X-ray generation portion, and wherein the cross-sectional area of the electron passage is increased toward at least the end thereof on the side closer to the target with a step-like change.

18. The X-ray generation apparatus according to claim 17, wherein an angle θ formed by the secondary X-ray generation portion and the target satisfies a following relationship of:

$$10° < \theta < 85°.$$

19. The X-ray generation apparatus according to claim 17, wherein the cross-sectional area of the electron passage is continuously increased toward at least the end thereof on the side closer to the target.

20. The X-ray generation apparatus according to claim 19, wherein the cross-sectional area of the electron passage is linearly increased toward at least the end thereof on the side closer to the target.

21. The X-ray generation apparatus according to claim 19, wherein the cross-sectional area of the electron passage is increased toward at least the end thereof on the side closer to the target such that a cross-section of the electron passage has an upwardly convex circular-arc shape.

22. The X-ray generation apparatus according to claim 19, wherein the cross-sectional area of the electron passage is increased toward at least the end thereof on the side closer to the target such that a cross-section of the electron passage has a downwardly convex circular-arc shape.

23. The X-ray generation apparatus according to claim 17, wherein at least a part of the X-ray generated upon the collision of the reflection electrons against the secondary X-ray generation portion transmits through a region of the target against which the electrons collide.

24. The X-ray generation apparatus according to claim 23, wherein the target is made of one of tungsten, tantalum and molybdenum.

25. The X-ray generation apparatus according to claim 23, wherein the secondary X-ray generation portion is made of one of tungsten, tantalum and molybdenum.

26. The X-ray generation apparatus according to claim 23, wherein the target is disposed on a surface of a support base, which surface is positioned to face the electron emission source.

27. The X-ray generation apparatus according to claim 26, wherein the support base is made of one of diamond, silicon nitride, and aluminum nitride.

28. The X-ray generation apparatus according to claim 17, wherein the electron emission source is disposed inside a vacuum vessel, and
the electron passage forming member is disposed in an opening of the vacuum vessel.

29. The X-ray generation apparatus according to claim 28, wherein the vacuum vessel is disposed in an envelope, and an insulating medium is filled in an empty space between the vacuum vessel and the envelope.

30. The X-ray generation apparatus according to claim 29, wherein a voltage control unit configured to output a voltage signal for controlling the generation of the X-ray is disposed inside the envelope.

31. A radiography system comprising:
the X-ray generation apparatus according to claim 17,
an X-ray detector configured to detect an X-ray having been radiated from the X-ray generation apparatus and having transmitted through a subject; and
a control unit configured to control the X-ray generation apparatus and the X-ray detector.

32. An X-ray generation apparatus of transmission type comprising:
an electron emission source; and
a target generating an X-ray with collision of electrons emitted from the electron emission source against the target,
wherein the X-ray generation apparatus further comprises a secondary X-ray generation portion generating an X-ray with collision of electrons reflected by the target against the secondary X-ray generation portion, and
the secondary X-ray generation portion and the target are arranged such that the X-ray generated with the direct collision of the electrons against the target and the X-ray generated with the collision of the electrons reflected by the target against the secondary X-ray generation portion are both radiated to an outside,
an electron passage surrounded by and formed in an electron passage forming member, and positioned on one side of the target closer to the electron emission source,
wherein the electrons emitted from the electron emission source collide against the target after passing through the electron passage,
wherein a cross-sectional area of the electron passage at least at an end thereof on a side closer to the target is larger than a cross-sectional area of the electron passage on a side farther away from the target, and at least a part of an inner wall surface of a region of the electron passage where the cross-sectional area thereof is increased serves as the secondary X-ray generation portion,
wherein the cross-sectional area of the electron passage is continuously increased toward at least the end thereof on the side closer to the target, and
wherein the cross-sectional area of the electron passage is linearly increased toward at least the end thereof on the side closer to the target.

33. The X-ray generation apparatus according to claim 32, wherein an angle θ formed by the secondary X-ray generation portion and the target satisfies a following relationship of:

$$10° < \theta < 85°.$$

34. The X-ray generation apparatus according to claim 32, wherein the cross-sectional area of the electron passage is increased toward at least the end thereof on the side closer to the target such that a cross-section of the electron passage has an upwardly convex circular-arc shape.

35. The X-ray generation apparatus according to claim 32, wherein the cross-sectional area of the electron passage is increased toward at least the end thereof on the side closer to the target such that a cross-section of the electron passage has a downwardly convex circular-arc shape.

36. The X-ray generation apparatus according to claim 32, wherein at least a part of the X-ray generated upon the collision of the reflection electrons against the secondary X-ray generation portion transmits through a region of the target against which the electrons collide.

37. The X-ray generation apparatus according to claim 36, wherein the target is made of one of tungsten, tantalum and molybdenum.

38. The X-ray generation apparatus according to claim 36, wherein the secondary X-ray generation portion is made of one of tungsten, tantalum and molybdenum.

39. The X-ray generation apparatus according to claim 36, wherein the target is disposed on a surface of a support base, which surface is positioned to face the electron emission source.

40. The X-ray generation apparatus according to claim 39, wherein the support base is made of one of diamond, silicon nitride, and aluminum nitride.

41. The X-ray generation apparatus according to claim 32, wherein the electron emission source is disposed inside a vacuum vessel, and
   the electron passage forming member is disposed in an opening of the vacuum vessel.

42. The X-ray generation apparatus according to claim 41, wherein the vacuum vessel is disposed in an envelope, and an insulating medium is filled in an empty space between the vacuum vessel and the envelope.

43. The X-ray generation apparatus according to claim 42, wherein a voltage control unit configured to output a voltage signal for controlling the generation of the X-ray is disposed inside the envelope.

44. A radiography system comprising:
   an X-ray generation apparatus according to claim 32,
   an X-ray detector configured to detect an X-ray having been radiated from the X-ray generation apparatus and having transmitted through a subject; and
   a control unit configured to control the X-ray generation apparatus and the X-ray detector.

* * * * *